(12) United States Patent
Kokones et al.

(10) Patent No.: US 8,634,934 B2
(45) Date of Patent: Jan. 21, 2014

(54) DIRECTIONAL LEAD ASSEMBLY

(75) Inventors: Scott Kokones, Boston, MA (US); John Swoyer, Andover, MN (US); Jesse Geroy, North St. Paul, MN (US)

(73) Assignee: Intelect Medical, Inc., Cleveland, OH (US)

( * ) Notice: Subject to any disclaimer, the term of this patent is extended or adjusted under 35 U.S.C. 154(b) by 170 days.

(21) Appl. No.: 13/207,012

(22) Filed: Aug. 10, 2011

(65) Prior Publication Data

US 2011/0301682 A1   Dec. 8, 2011

Related U.S. Application Data

(63) Continuation of application No. 12/029,896, filed on Feb. 12, 2008, now Pat. No. 8,019,440.

(51) Int. Cl.
*A61N 1/05* (2006.01)

(52) U.S. Cl.
USPC .......................................................... 607/116

(58) Field of Classification Search
USPC .......................................................... 607/116
See application file for complete search history.

(56) References Cited

U.S. PATENT DOCUMENTS

| | | | |
|---|---|---|---|
| 4,848,352 A | 7/1989 | Pohndorf et al. | |
| 5,000,194 A | 3/1991 | van den Honert et al. | |
| 5,172,694 A | 12/1992 | Flammang et al. | |
| 5,405,375 A | 4/1995 | Ayers et al. | |
| 5,450,846 A | 9/1995 | Goldreyer | |
| 5,458,629 A | 10/1995 | Baudino et al. | |
| 5,711,316 A | 1/1998 | Elsberry et al. | |
| 5,713,922 A | 2/1998 | King | |
| 5,938,688 A | 8/1999 | Schiff | |
| 6,125,302 A | 9/2000 | Kuzma | |
| 6,167,311 A | 12/2000 | Rezai | |
| 6,522,904 B1 | 2/2003 | Mika et al. | |
| 6,757,970 B1 | 7/2004 | Kuzma et al. | |
| 7,047,082 B1* | 5/2006 | Schrom et al. | 607/116 |
| 7,047,084 B2* | 5/2006 | Erickson et al. | 607/116 |
| 7,096,070 B1* | 8/2006 | Jenkins et al. | 607/116 |
| 7,212,867 B2* | 5/2007 | Van Venrooij et al. | 607/116 |
| 7,346,382 B2 | 3/2008 | McIntyre et al. | |
| 8,019,440 B2* | 9/2011 | Kokones et al. | 607/116 |
| 2002/0183817 A1 | 12/2002 | Van Venrooij et al. | |
| 2004/0098074 A1 | 5/2004 | Erickson et al. | |
| 2005/0015130 A1 | 1/2005 | Gill | |
| 2005/0177039 A1 | 8/2005 | Mills et al. | |
| 2005/0246004 A1* | 11/2005 | Cameron et al. | 607/116 |
| 2006/0017749 A1 | 1/2006 | McIntyre et al. | |
| 2006/0025841 A1 | 2/2006 | McIntyre | |
| 2007/0168008 A1 | 7/2007 | Olsen | |
| 2008/0215101 A1 | 9/2008 | Rezai et al. | |

OTHER PUBLICATIONS

European Patent Office, the International Search Report and the Written Opinion of the International Searching Authority in Application No. PCT/US2009/031484, dated Mar. 30, 2009.

* cited by examiner

*Primary Examiner* — Kennedy Schaetzle

(74) *Attorney, Agent, or Firm* — Kenyon & Kenyon LLP

(57) ABSTRACT

Leads having directional electrodes thereon. Also provided are leads having directional electrodes as well as anchoring prongs to secure the electrodes to the leads. Also provided are leads with directional electrodes where all the electrodes have the same surface area. Methods of treating conditions and selectively stimulating regions of the brain such as the thalamus and cerebellum are also provided.

28 Claims, 6 Drawing Sheets

DIRECTIONAL LEAD ASSEMBLY

CROSS REFERENCE TO RELATED APPLICATION

This application is a continuation of U.S. Ser. No. 12/029,896, filed Feb. 12, 2008, now U.S. Pat. No. 8,019,440, which is hereby incorporated by reference in its entirety.

FIELD OF INVENTION

The present invention provides an implantable or insertable electrical lead having directional electrodes thereon.

BACKGROUND

Neuromodulation, such as deep brain stimulation, is becoming an increasingly preferred form of therapy for certain neurological conditions and disorders. Currently, deep brain stimulation of the subthalamic nucleus and the globus pallidus interna is approved for treatment of Parkinson's disease and deep brain stimulation of the ventral intermediate nucleus is approved for treatment of essential tremor. Other target sites in the brain to treat additional disorders are also contemplated. For example, as described in U.S. Pat. No. 5,938,688 and U.S. Pat. No. 6,167,311, respectively, the intralaminar nuclei of the thalamus could be stimulated to treat patients with impaired cognitive function and/or patients with psychological disorders.

Current electrical leads used in deep brain stimulation, however, do not provide precise targeting of the areas of the thalamus such as the intralaminar nuclei, such that the desired volume of tissue is stimulated. Accordingly, there is a need in the art for a stimulation device that precisely targets specific regions of the thalamus, maximizes stimulation of these specific regions and minimizes stimulation of adjacent tissue that results in undesirable side effects.

SUMMARY

In one embodiment, the present invention provides a lead comprising a cylindrical lead body having a plurality of directional electrodes on a distal end thereof. Preferably, the plurality of directional electrodes are between four to twelve electrodes. The cylindrical lead body further comprises at least one anchoring prong attached to each electrode to anchor the electrode to the cylindrical lead body.

In another embodiment, the present invention provides an electrical lead comprising a cylindrical lead body having a plurality of directional electrodes disposed on a distal end thereof, wherein each one of the plurality of directional electrodes has the same surface area.

In another embodiment, a lead has any one of, all of, or any combination of the following features: a cylindrical lead body having a diameter of about 0.70 millimeters (mm) to about 1.5 mm; four to twelve directional electrodes disposed on the outer surface of the cylindrical lead body; each electrode spanning about 90° to about 150° circumferentially around the body; each electrode being radially spaced apart from an adjacent electrode by 30° to 180°; each electrode being axially spaced apart from an adjacent electrode by 0.25 mm to 2.00 mm; each electrode having a surface areas of between about 1 mm² to 7 mm²; and each electrode having a length of about 0.75 mm to 3.0 mm. Preferably, the cylindrical lead body further comprises at least one anchoring prong attached to each electrode for anchoring the electrode to the cylindrical lead body.

In a preferred embodiment, the lead comprises a cylindrical body having electrodes thereon that comprises any one of, all of, or any combination of the following features: a cylindrical lead body having a diameter of about 1.27 mm, eight electrodes disposed on the outer surface of the cylindrical lead body; each electrode spanning about 120° circumferentially around the cylindrical body; each electrode being radially spaced apart from an adjacent electrode by 60°; each electrode being axially spaced apart from an adjacent electrode by 0.50 mm; each electrode having a surface area of about 1.27 mm²; and each electrode having a length of about 2.25 mm. The cylindrical lead body further comprises at least one anchoring prong attached to each electrode for anchoring the electrode to the cylindrical lead body.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

The present invention provides electrical leads comprising a cylindrical lead body having directional electrodes disposed on a distal end thereof. As used herein, a "directional electrode" refers to an electrode on a lead body, in which the electrode extends less than 360° about the lead body.

Figure 1:
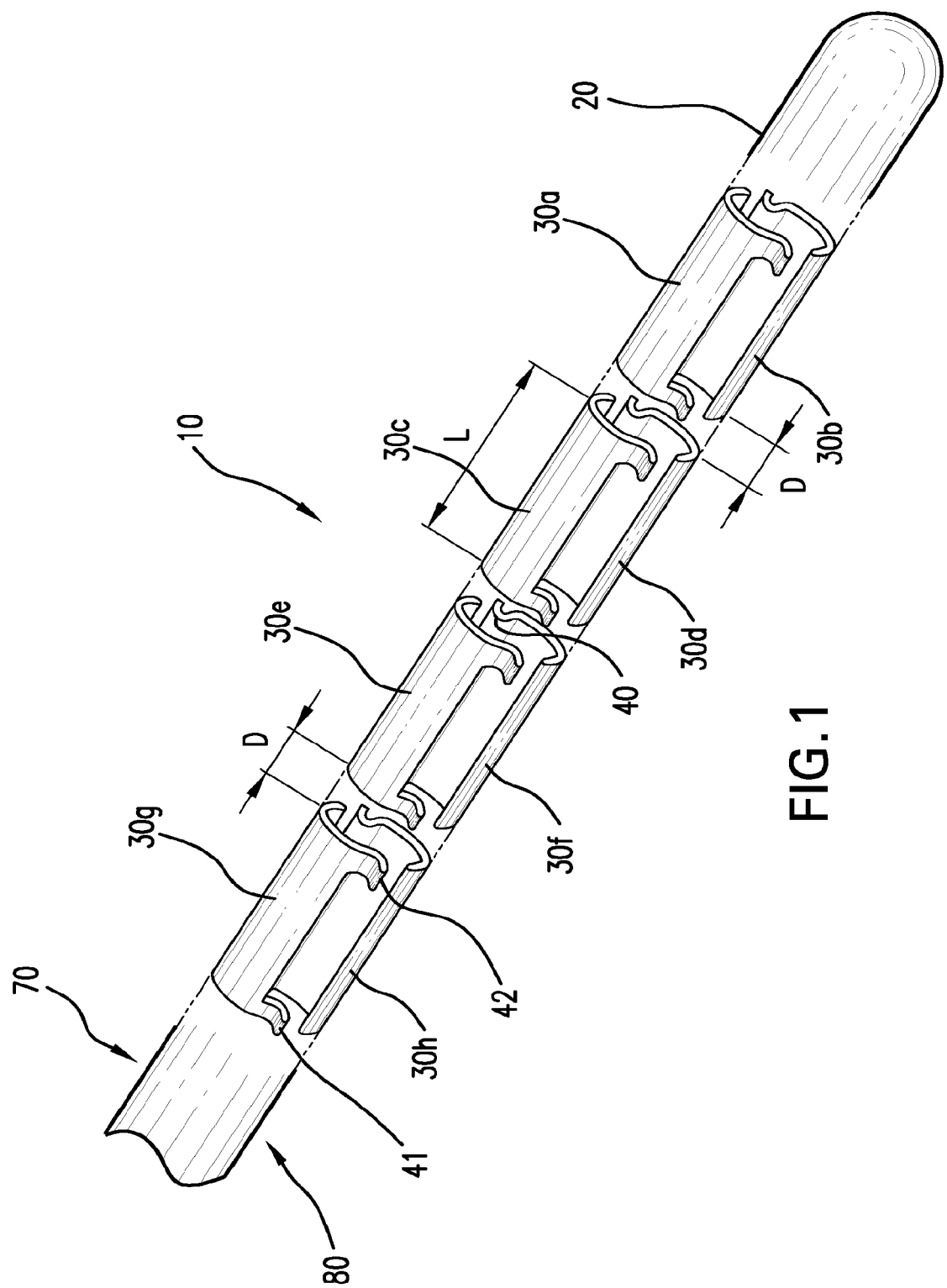
FIG. 1 is a fragmented schematic drawing of a distal end of a lead with electrodes disposed thereon.

FIG. 1 shows an embodiment of electrical lead 10 comprising a cylindrical lead body 20 having a plurality of directional electrodes 30a-30h thereon. In FIG. 1, each electrode of a pair of electrodes is disposed directly opposite from the other, on opposing sides, first side 70 and second side 80, of the lead body 20. Additionally, the adjacent pairs can be aligned with each other, as shown in FIG. 1 and FIG. 2, or rotated relative to each other, as shown in FIG. 3.

Figure 2:
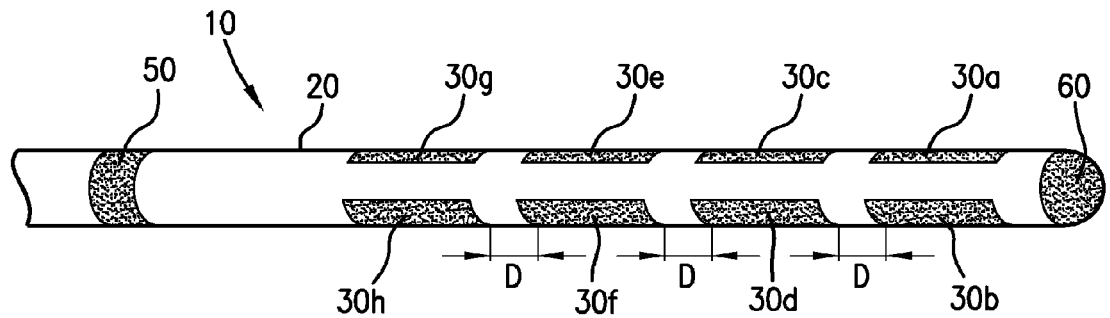
FIG. 2 is a fragmented schematic drawing of a distal end of another embodiment of a lead with electrodes disposed thereon.

FIG. 2 additionally shows an electrode 60 that can be located on the distalmost tip of the lead body, and at least one band electrode 50 can be provided near the proximal end of the lead body 20. The distal electrode 60 can be one unitary electrode or two separate electrodes and can be used for stimulating or sensing in a region of the brain. The band electrode 50 is spaced away from the directional electrodes 30, to provide for stimulation or sensing in a region of the brain different from the region of the brain to which the directional electrodes apply electrical stimulation. For example, band electrode 50 can provide stimulation or sense activity in the cortical region of the brain. Of course, both a distalmost electrode and a proximal band electrode need not be provided; the electrical lead body can include one or the other, as shown in the below described embodiments.

Figure 3:
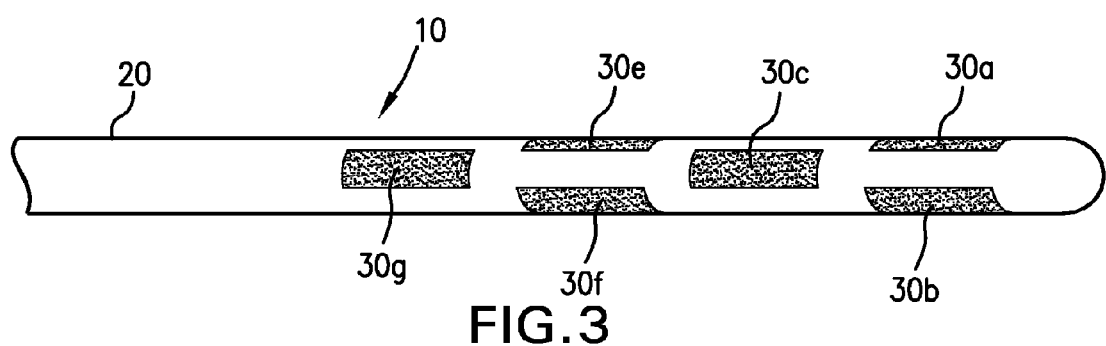
FIG. 3 is a fragmented schematic drawing of a distal end of another embodiment of a lead with electrodes disposed thereon.
Figure 15:
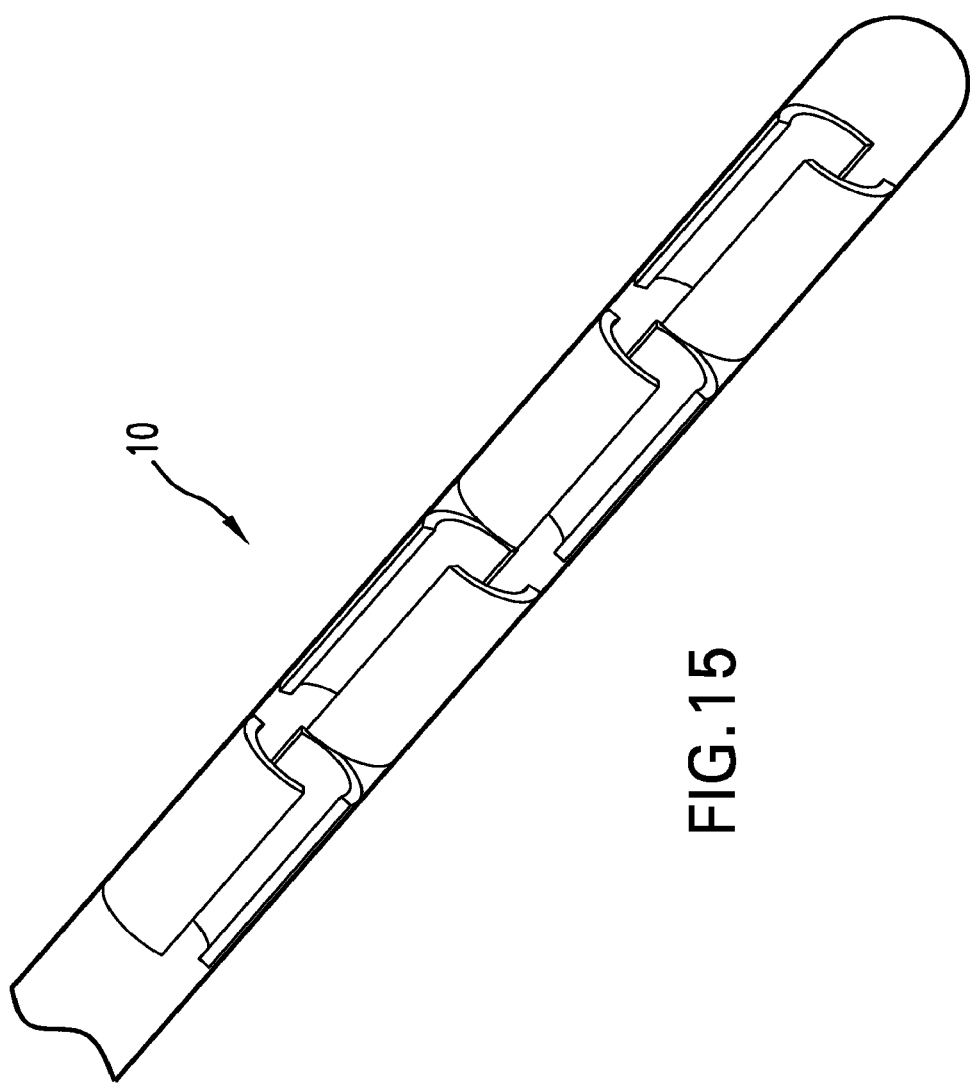
FIG. 15 is a fragmented schematic drawing of a distal end of another embodiment of a lead with electrodes disposed thereon, where the lead is shown as translucent in order to view the electrodes on both sides of the lead.

FIG. 3 shows an electrical lead 10 with a first pair of electrodes 30a and 30b being rotated 90° relative to a second pair of electrodes 30c and 30d (not visible in this view). FIG. 3 also shows a third pair of electrodes 30e and 30f being rotated 90° relative to the second pair of electrodes 30c and 30d, and thus being aligned with the first pair of electrodes 30a and 30b. Additionally, FIG. 3 shows a fourth pair of electrodes 30g and 30h (not visible in this view) being rotated 90° relative to the third pair of electrodes 30e and 30f, and thus being aligned with the second pair of electrodes 30c and 30d. Although a rotation of about 90° is shown in FIG. 3, the adjacent pairs can be rotated between about 10° to 90° relative to each other. Further, although in this embodiment, electrode lead 10 has four pairs of electrodes, the electrode lead 10 can have greater or fewer electrodes. Additionally, in one embodiment, no electrode pairs are aligned with each other, thus creating a spiral configuration, as shown in FIG. 15.

Figure 4:
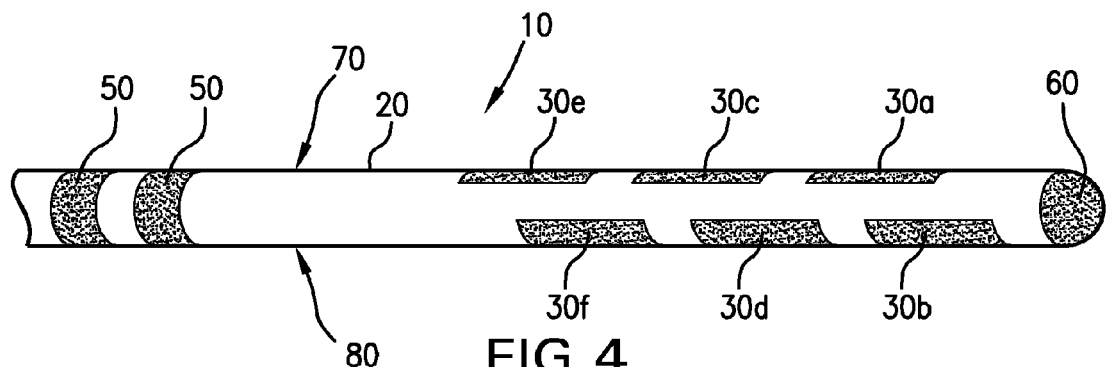
FIG. 4 is a fragmented schematic drawing of a distal end of another embodiment of a lead with electrodes disposed thereon.
Figure 5:
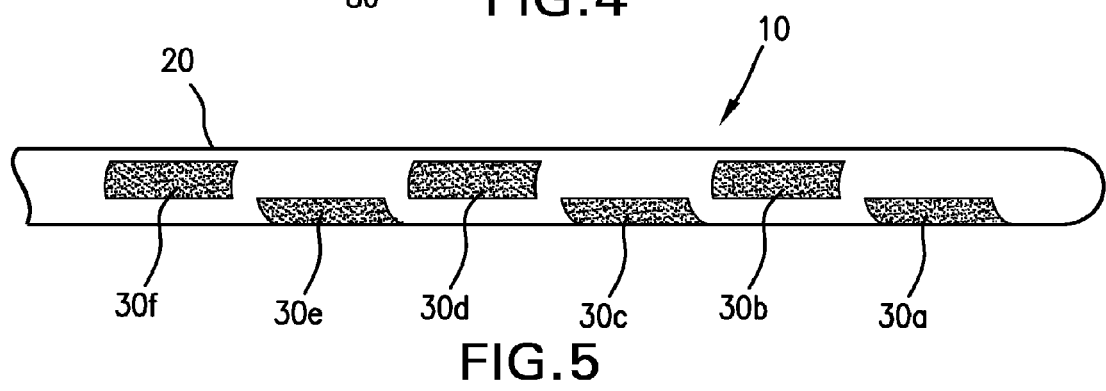
FIG. 5 is a fragmented schematic drawing of a distal end of another embodiment of a lead with electrodes disposed thereon.

The electrodes can also be arranged singly, as shown in FIG. 4 and FIG. 5. FIG. 4 is similar to the embodiment of FIG. 2, however the electrodes 30a, 30c and 30e on the first side 70 of the lead body 20 are shifted longitudinally with respect to the electrodes 30b, 30d, 30f on the second side 80 of the lead body 20. Thus, there is no pairing of the electrodes. The electrodes 30a, 30c, and 30e on the first side 70 of the lead body 20 are disposed at least partially opposite the space between the electrodes on the second side 80 of the lead body 20. Specifically, electrode 30a is disposed opposite partial portions of electrode 30b and electrode 30d, and the entire space between electrode 30b and electrode 30d; electrode 30c is disposed opposite partial portions of electrode 30d and electrode 30f, and the entire space between electrode 30d and electrode 30f; and electrode 30e is disposed opposite electrode 30f and a partial portion of the space distal of electrode 30f. The lead shown in FIG. 4 also includes two optional band electrode 50 near the proximal end of the lead body 20, which could be used, for example, for sensing or stimulating the cortical region of the brain. Of course these two band electrodes could also be disposed on the other lead embodiments described herein.

FIG. 5 shows electrodes 30a-30f arranged singly, spaced along the longitudinal axis. Each electrode can be rotated between about 10° to 90° relative to each adjacent electrode to provide for directed stimulation on only one side of the lead body 20. Alternatively, the adjacent electrodes can be arranged in a spiral configuration ascending the lead body 20.

Figure 6:
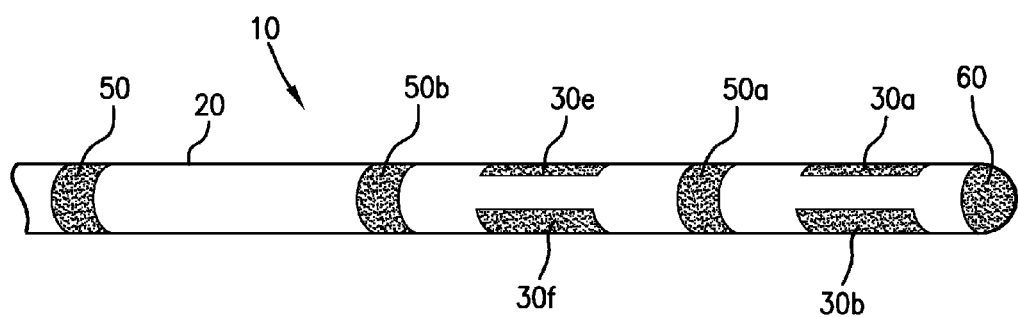
FIG. 6 is a fragmented schematic drawing of a distal end of another embodiment of a lead with electrodes disposed thereon.

FIG. 6 shows an electrical lead 10 with band electrodes 50 arranged in an alternating configuration between directional electrodes 30. FIG. 6 is similar to the embodiment of FIG. 2, however the second pair of directional electrodes 30c, 30d and the fourth pair of directional electrodes 30g, 30h are both replaced by band electrodes 50a, 50b. FIG. 6 shows two pair of electrodes directional 30a, 30b and directional electrodes 30e, 30f, and two band electrodes 50a, 50b between the pairs of directional electrodes 30, a distalmost electrode 60, and a proximal band electrode 50. However, the electrical lead 10 can have a different number of directional electrode pairs and a different number of band electrodes between the directional electrode pairs.

Figure 7:
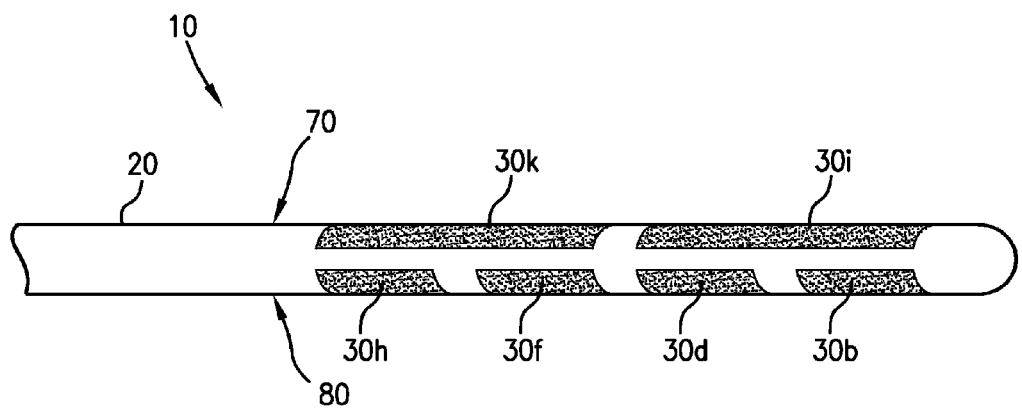
FIG. 7 is a fragmented schematic drawing of a distal end of another embodiment of a lead with electrodes disposed thereon.

FIG. 7 shows an electrical lead 10 with directional electrodes 30 on the first side 70 of the lead body 20 have a length L that is greater than the length L of the directional electrodes 30 on the second side 80 of the lead body 20. Preferably, the length and radial spanning is modified such that the surface area of each of the electrodes 30 is about 3 mm². FIG. 7 is similar to the embodiment of FIG. 2, however the two electrodes 30a and 30c are replaced by one electrode 30i having a length L that approximately equals (the length L of 30b)+(the length L of 30d)+(the distance D between 30b and 30d) and the two electrodes 30e and 30g are replaced by one electrode 30k having a length L that approximately equals (the length L of 30f)+(the length L of 30h)+(the distance D between 30f and 30h). Of course, electrodes 30i and 30k could have other lengths as well and the lead could have another number of electrodes disposed thereon.

As shown in FIG. 1 and FIGS. 8-13, in certain embodiments, the cylindrical body includes at least one anchoring prong 41, 42, 43, 44 and/or 45 attached to or otherwise integral with each electrode 30 that is encased in the lead body 20 during manufacturing to anchor the electrodes 30 to the body 20. Electrodes 30 can also be treated with a solvent, such as toluene or DMAC, to aid in adhering to the lead body 20. The lead body 20 is preferably injection molded using polyurethane or other biocompatible materials.

Figure 8:
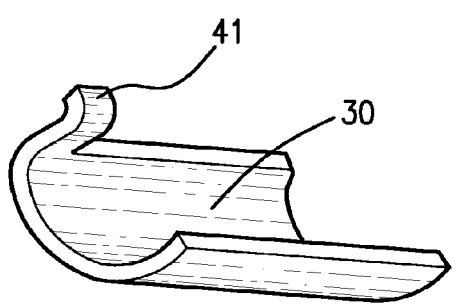
FIG. 8 shows an embodiment of an electrode with an anchoring prong attached thereto.
Figure 9:
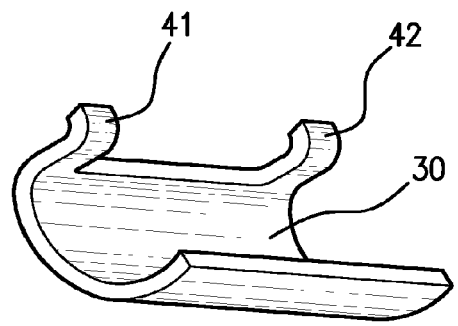
FIG. 9 shows another embodiment of an electrode with anchoring prongs attached thereto.
Figure 10:
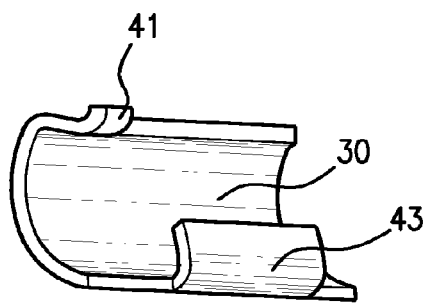
FIG. 10 shows another embodiment of an electrode with anchoring prongs attached thereto.
Figure 11:
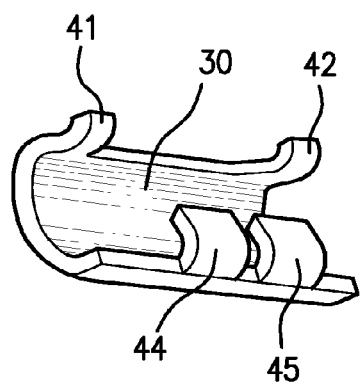
FIG. 11 shows another embodiment of an electrode with anchoring prongs attached thereto.
Figure 12:
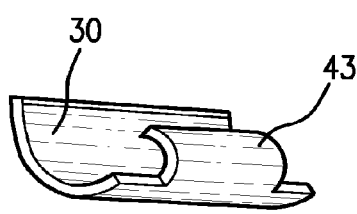
FIG. 12 shows another embodiment of an electrode with anchoring prongs attached thereto.
Figure 13:
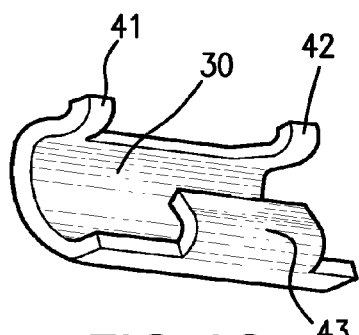
FIG. 13 shows another embodiment of an electrode with anchoring prongs attached thereto.

FIGS. 8-13 show different configurations of anchoring prongs on the electrode 30. FIG. 8 shows an electrode 30 with one prong 41 at one end of one length side. FIG. 9 shows an electrode 30 with two prongs 41, 42, one at each end of one length side. FIG. 10 shows an electrode 30 with one prong 41 at one end of one length side and a second prong 43 at the center of the other length side. FIG. 11 shows an electrode 30 with two prongs 41, 42, one at each end of one length side and two prongs 44, 45 at the center of the other length side. FIG. 12 shows an electrode 30 with one prong 43 at the center of one length side. FIG. 13 shows an electrode 30 with one prong 41, 42, one at one end of one length side and a third prong 43 at the center of the other length side. Other different permutations and combinations of anchoring prongs are also contemplated. Preferably, each electrode has at least one prong on each length side to prevent the electrode 30 from lifting off of the electrode body 20.

In any of the embodiments described above, the size, shape, configuration, and dimensions of the elongate lead will vary depending upon the particular application. For example, the shape of the elongate lead may be cylindrical, flat, conical, etc. Where the elongate lead is cylindrical, the cylindrical lead body has a diameter of about 0.70 mm to 1.5 mm. In a preferred embodiment, the cylindrical lead body has a diameter of about 1.27 mm. Other diameters are also possible, depending, for example, upon the particular application.

Further, the material composition; electrical properties (e.g., impedance); dimensions and configurations (such as, for example, height, width, axial spacing, and shape); number; and arrangement of the stimulation electrodes on the elongate lead will vary depending upon the particular application. For example, the electrodes may have a cylindrical shape, an oval shape, or a rectangular shape. In fact, the individual electrodes may take any variety of shapes to produce the desired focused and/or directional electric field.

Regarding the number of electrodes, in certain embodiments, the cylindrical body has four to twelve electrode disposed thereon. In a preferred embodiment, the cylindrical body has eight electrodes disposed thereon. The cylindrical lead body could also have other numbers of electrodes disposed thereon.

As denoted in FIG. 1, each electrode is approximately rectangular, having two length sides, each with a length L, and two width sides, each with a width W, which is also referred to herein as the "radial spanning." The length sides are approximately parallel to the longitudinal axis of the cylindrical lead body and the width sides are approximately perpendicular to the longitudinal axis of the cylindrical lead body. In certain embodiments, the length of each electrode is about 0.75 mm to 3.0 mm. In a preferred embodiment, the length of the electrode is about 2.25 mm. Of course, the electrodes could also have other dimensions. In certain embodiments, the surface area of each electrode is between about 1 $mm^2$ to 7 $mm^2$. In a preferred embodiment, the surface area of each electrode is about 3 $mm^2$, such that the charge density and safety calculations are the same for all electrodes. In other particularly preferred embodiments, all the electrodes have the same surface area irrespective of the particular shape or configuration of the electrode. For example, in embodiments where the cylindrical lead body has both cylindrical ring electrodes disposed thereon and directional electrodes disposed thereon, in this embodiment, the surface area of both types of electrodes are the same. Of course, it is understood that each electrode does not need to have the same surface area and certain electrodes can have different surface areas.

As seen in the above-described embodiments, the directional electrodes do not form a continuous electrode surface, but rather the electrode surface is segmented into a plurality of individual electrodes that are substantially isolated from each other. Individual directional electrodes can range in an angular distance around the exterior of the body of the elongate lead by as little as a few degrees to almost completely around the body of the lead. In certain embodiments, a directional electrode is curved around the cylindrical body 10 so that the electrode radially spans approximately 90° to 150° about the circumference of the lead body 20 and each electrode is radially spaced apart from an adjacent electrode by 30° to 180°. In a preferred embodiment, the electrode extends about 120° of the circumference of the lead body and the electrodes are radially spaced 60° apart. Of course other configurations for the radial span and radial spacing of the electrodes are also contemplated.

Regarding the axial spacing of the electrodes, in certain embodiments, the plurality of electrodes are spaced along the longitudinal axis at a distance D, as denoted in FIG. 1, of 0.25 mm to 2.00 mm from the next adjacent electrode. In a preferred embodiment, the distance D is about 0.5 mm. Other configurations for the axial spacing between adjacent electrodes is also contemplated. The electrodes can each be longitudinally spaced the same distance apart or the distance between the electrodes can be varied. Further, the electrodes can be disposed singly or in pairs around the circumference of the lead body.

The material composition and mechanical properties (i.e. the flexibility) of the body of the elongate lead will vary depending upon the particular application. In some cases, the body of the elongate body is formed of a non-conductive material, such as a polymeric material, glass, quartz or silicone. In a preferred embodiment, the elongate lead is fabricated from polyurethane.

The electrodes can be fabricated from a number of suitable materials including platinum or titanium. In a preferred embodiment, the electrodes are fabricated from platinum iridium.

Figure 14:
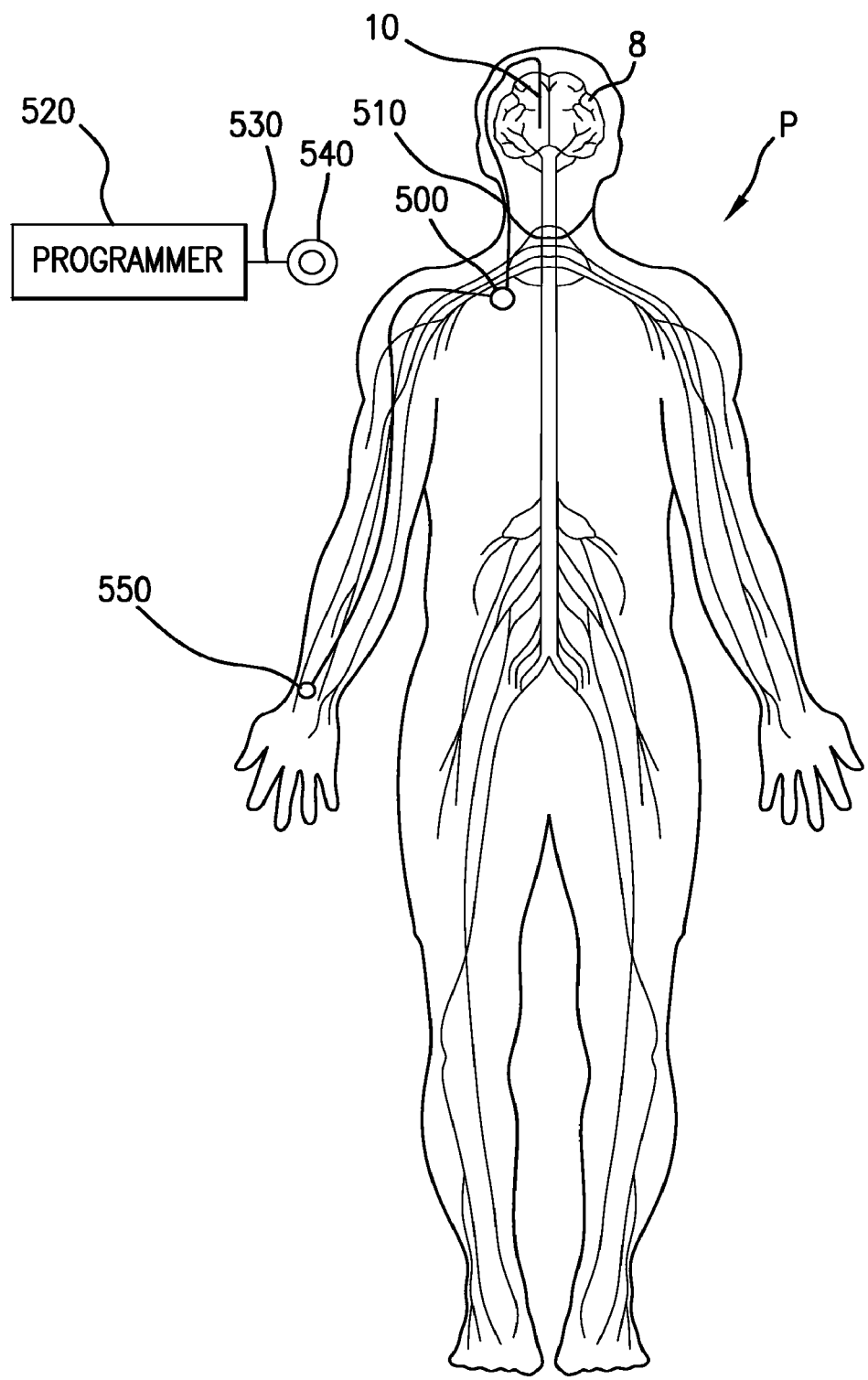
FIG. 14 is a diagrammatic view of a patient in which an embodiment of a lead according to the present invention has been implanted.

Electrical lead 10 can be implanted or inserted and removed to modulate specific regions of the body. In certain embodiments, the modulation includes ablation, stimulation and/or inhibition of certain regions of the body. In a preferred embodiment, an electrical lead is used to modulate a part of the nervous system, including the brain and spinal cord. In a more preferred embodiment, an electrical lead is used to modulate the brain. In still another more preferred embodiment, an electrical lead is used to modulate the thalamus 8, as schematically illustrated in FIG. 14 or the cerebellum. For example, activation of electrode 30 can result in a volume of activation V that reaches the intralaminar nuclei as well as parts of the lateral, medial and anterior thalamus. Although the parameters of stimulation can depend on a number of factors, in certain embodiments, a volume of activation is generated by 3V, 90 microsecond, and approximately 50 hertz stimulation.

Depending on the particular therapeutic application, different electrodes 30 and/or different combinations of electrodes 30 on electrical lead 10 can be activated to provide different directional modulation of specific regions brain, such as the thalamus, and more particularly the lateral thalamus and/or the medial thalamus as well as nuclei within the lateral and/or medial thalamus, such as the intralaminar nuclei. Electrical lead 10 is also capable of stimulating both the lateral and medial thalamus.

Although not limited to any particular areas of the thalamus, the electrical lead 10 of the present invention is particularly useful for modulating the intralaminar nuclei, which include, for example, the centromedial nucleus, the parafascicular nucleus, the paracentral nucleus, the central lateral nucleus, and the central medial nucleus. The electrical lead 10 may also be used for preferential modulation of one side or the other side of nuclei or a nucleus split by the internal medullary lamina.

Electrodes 30 of the present invention can have adjustable power. For example, the pulsing parameters of the electrodes 30 may be adjusted to initiate, stop, increase, or decrease the pole combinations, energy, amplitude, pulse width, waveform shape, frequency, and/or voltage or any other pulsing parameter known to one of skill in the art to adjust the degree of modulation delivered thereby. In a preferred embodiment, each electrode 30 of body 20 of lead 10 is selectively controllable such that the pulsing parameters of an electrode 30 can be adjusted independent of the pulsing parameters of another electrode 30.

Referring to FIG. 14, the selective control over each electrode 30 may be achieved by employing a system including a programmer 520 coupled via a conductor 530 to a telemetry antenna 540. The programmer 520 is capable of sending signals via the telemetry antenna 540 to control the electrical signal delivered to electrodes 30. Such a system permits the selection of various pulse output options after lead 10 is implanted using telemetry communications. The present invention also contemplated radio-frequency systems to selectively power electrodes 30.

As will be understood by one of skill in the art, the independent control of each electrode 30 also provides a practitioner with another means of modify or steer the direction of stimulation since the locus of modulation can be selectively adjusted to precisely target portions of the thalamus to achieve the desired therapy. For example, electrode 30a may be powered to modulate an area adjacent thereto while the signal to electrode 30c may be substantially minimized to reduce or stop modulation to an area adjacent to electrode 30c. Because the locus of modulation can be selectively adjusted and/or steered in this embodiment of lead 10, specific target areas can be precisely targeted to achieve the desired therapy. Other or additional means of selectively steering electrical modulation may also be utilized in the present invention, such as the methods described in U.S. Pat. No. 5,713,922, which is incorporated by reference herein.

A neural modulation delivery system including lead 10 to modulate neural tissue to affect a neurological condition may include other components useful in identifying, monitoring, or affecting a specific site or a particular neurological condition associated with the specific thalamic site. For example, such a system could include a component for lesioning and temperature monitoring, and/or a component that has a fiberoptic monitor which allows telemetric intracranial monitoring capabilities, and/or a microelectrode recording component, and/or a sensing component to incorporate a feedback mechanism to assist in determining whether lead 10 should be adjusted. With respect to a sensing component, referring to FIG. 14, a sensor 550 can be incorporated with a system of stimulating the thalamus, for example, according to the present invention. Sensor 550 can be used with a closed-loop feedback system in order to automatically determine the level of stimulation necessary to provide the desired therapy. Sensor 550 may be implanted into a portion of a patient P's body suitable for detecting characteristics, symptoms or attributes of the condition or disorder being treated such as electrical brain activity, cerebral blood flow, and/or vital signs or other chemical and electrical activity of the body. Sensors suitable for use in a system according to the present invention include, for example, those disclosed in U.S. Pat. No. 5,711,316, which is incorporated by reference herein. In cases where the attribute of the symptom is the electrical activity of the brain, stimulating electrodes may be intermittently used to record electrical activity. Alternatively, one or more electrodes implanted within the brain may serve as a sensor or a recording electrode. When necessary, these sensing or recording electrodes may deliver modulation therapy to the thalamus, for example. The output of an external feedback sensor may communicate with an implanted pulse generator through a telemetry down-link.

In order to advance lead 10 through a cannula, an actuator system that creates linear motion may be provided. Lead 10 may be provided within the cannula as part of the device or lead 10 may be installed during the surgical technique. Preferably, lead 10 is capable of being bent, capable of being pre-bent such that lead 10 has a memory bend, or capable of being pre-formed into a desired shape that has memory. For example, lead 10 may be fabricated from a shape memory alloy such as nitinol.

The present invention contemplates that electrical lead 10 is not only capable of being adjusted intra-operatively, but also is capable of being adjusted post-operatively. Specifically, lead 10 positioning may be physically adjusted (advanced, retracted, or moved to a different location) in the brain post-operatively through the use of telemetry, RF signals, or other systems known in the art. The cannula which is used to insert the lead need only be inserted once while lead 10 may be repositioned in the brain tissue multiple times to reach the desired area of the brain. Further, electrodes 30 on lead 10 may be adjusted post-operatively by turning them on or off, adjusting the voltage, adjusting the frequency, and adjusting other electrical signal parameters trough the use of telemetry, RF signals, or other systems known in the art. Those skilled in the art will appreciate that electrical properties of the electrodes 30 and the resulting electrical field may be varied by selectively powering individual or groups of electrodes 30 formed from or controlled by micro-electrical mechanical systems (MEMS). Moreover, MEMS actuators may drive electrodes, drug delivery catheters, sensing probes, and the like to the desired locations in an area of interest. Furthermore, lead 10 may also be used in conjunction with brain stimulation modeling systems as described in U.S. Pat. No. 7,346,382, entitled "Brain Stimulation Models, Systems, Devices, and Methods", which is incorporated by reference herein.

The leads of the present invention can be used to treat a variety of medical conditions such as, for example, chronic pain, psychiatric disorders, traumatic brain injury, stroke and the present invention provides for such methods. For example, in certain embodiments a method of treating a medical condition comprises inserting or implanting an electrical lead according to an embodiment of the present invention in a target site of the body and selectively activating one or more of the directional electrodes to provide targeted stimulation of the target site. Further diseases are mention in co-pending U.S. utility application Ser. No. 11/871,727, filed on Oct. 12, 2007, U.S. Patent Publication No. 2008/0215101, which is incorporated by reference herein.

The leads of the present invention can be used to treat a variety of medical conditions such as, for example, chronic pain, psychiatric disorders, traumatic brain injury, stroke and the present invention provides for such methods. For example, in certain embodiments a method of treating a medical condition comprises inserting or implanting an electrical lead according to an embodiment of the present invention in a target site of the body and selectively activating one or more of the directional electrodes to provide targeted stimulation of the target site. Further diseases are mention in co-pending U.S. utility application Ser. No. 11/871,727, filed on Oct. 12, 2007, which is incorporated by reference herein.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:
1. An electrical lead comprising:
   a cylindrical lead body having an outer surface, a proximal end, a distal end and a longitudinal axis extending therethrough;
   a plurality of directional electrodes disposed on the distal end of the outer surface of the cylindrical lead body, wherein the plurality of electrodes comprises a first pair of electrodes and a second pair of electrodes, and wherein the second pair of electrodes is rotated relative to the first pair of electrodes; and
   at least one cylindrical band electrode extending around at least approximately an entirety of the circumference of the outer surface of the lead body and configured to one of operate as a sensor and perform an anatomical stimulation.

2. The electrical lead of claim 1, wherein the second pair of electrodes is rotated about 10° to 90° relative to the first pair of electrodes.

3. The electrical lead of claim 1, wherein the first pair of electrodes comprises a first electrode disposed about 180° relative to a second electrode, and the second pair of electrodes comprises a third electrode disposed about 180° relative to a fourth electrode.

4. The electrical lead of claim 3, wherein the plurality of electrodes further comprises: a third pair of electrodes comprising a fifth electrode disposed about 180° relative to a sixth electrode.

5. The electrical lead of claim 4, wherein the plurality of electrodes further comprises: a fourth pair of electrodes comprising a seventh electrode disposed about 180° relative to a eighth electrode.

6. The electrical lead of claim 5, wherein the second pair of electrodes is rotated 90° relative to the first pair of electrodes, the third pair of electrodes is rotated 90° relative to the second pair of electrodes, or the fourth pair of electrodes is rotated 90° relative to the third pair of electrodes.

7. The electrical lead of claim 4, wherein the first pair of electrodes and the third pair of electrodes are circumferentially aligned.

8. The electrical lead of claim 5, wherein the second pair of electrodes and the fourth pair of electrodes are circumferentially aligned.

9. The electrical lead of claim 1, further comprising at least one anchoring prong attached to or otherwise integral with each directional electrode of the plurality of directional electrodes to anchor the directional electrode to the cylindrical lead body.

10. An electrical lead comprising:
    a cylindrical lead body having an outer surface, a proximal end, a distal end and a longitudinal axis extending therethrough; and
    a plurality of directional electrodes disposed on the distal end of the outer surface of the cylindrical lead body, wherein one of:
       the plurality of electrodes comprises a first electrode disposed on a first side of the lead body and a second electrode that (a) shares with the first electrode at least one cross-section of the cylindrical body, which cross-section is perpendicular to the longitudinal axis of the cylindrical lead body; and (b) is (i) disposed on a second side of the lead body and (ii) shifted longitudinally with respect to the first electrode; and
       no cross-section of the cylindrical lead body that is perpendicular to the longitudinal axis of the cylindrical lead body includes a portion of more than one of the directional electrodes.

11. The electrical lead of claim 10, wherein the plurality of electrodes includes the first and second electrodes, and the first electrode is disposed about 180° relative to the second electrode.

12. The electrical lead of claim 11, wherein the plurality of electrodes further comprises: a third electrode being disposed about 180° relative to a fourth electrode, wherein at least a portion of the first electrode is longitudinally disposed directly opposite a space between the second electrode and the fourth electrode.

13. The electrical lead of claim 12, wherein the plurality of electrodes further comprises: a fifth electrode being disposed about 180° relative to a sixth electrode, wherein at least a portion of the third electrode is longitudinally disposed directly opposite a space between the fourth electrode and the sixth electrode.

14. The electrical lead of claim 13, wherein the first electrode, the third electrode, and the fifth electrode are circumferentially aligned on the first side of the lead body.

15. The electrical lead of claim 13, wherein the second electrode, the fourth electrode, and the sixth electrode are circumferentially aligned on the second side of the lead body.

16. The electrical lead of claim 10, wherein there is no spatial pairing of the plurality of directional electrodes.

17. The electrical lead of claim 10, further comprising at least one anchoring prong attached to or otherwise integral with each directional electrode of the plurality of directional electrodes to anchor the directional electrode to the cylindrical lead body.

18. An electrical lead configured to produce an anatomical stimulation, the electrical lead comprising
    a cylindrical lead body having an outer surface, a proximal end, a distal end and a longitudinal axis extending therethrough;
    a plurality of directional electrodes disposed on the distal end of the outer surface of the cylindrical lead body, wherein the plurality of electrodes comprises a first pair of electrodes and a second pair of electrodes, wherein the first pair of electrodes comprises a first electrode disposed about 180° relative to a second electrode, and wherein the second pair of electrodes comprises a third electrode disposed about 180° relative to a fourth electrode; and
    at least one cylindrical band electrode (a) extending around at least approximately an entirety of the circumference of the outer surface of the lead body, (b) disposed longitudinally between the first pair of electrodes and the second pair of electrodes, and (c) configured to one of operate as a sensor and perform an anatomical stimulation.

19. The electrical lead of claim 18, further comprising at least one band electrode spaced proximally of the plurality of directional electrodes.

20. The electrical lead of claim 18, further comprising at least one anchoring prong attached to or otherwise integral with each directional electrode of the plurality of directional electrodes to anchor the directional electrode to the cylindrical lead body.

21. An electrical lead comprising:
    a cylindrical lead body including an outer surface, a proximal end, a distal end and a longitudinal axis extending therethrough;
    a plurality of directional electrodes disposed on the distal end of the outer surface of the cylindrical lead body, wherein the plurality of electrodes comprises a first pair of electrodes and a second pair of electrodes, and wherein the second pair of electrodes is rotated relative to the first pair of electrodes; and an electrode spanning a distalmost edge of the cylindrical lead body.

22. The electrical lead of claim 21, wherein the second pair of electrodes is rotated about 10° to 90° relative to the first pair of electrodes.

23. The electrical lead of claim 21, wherein the first pair of electrodes comprises a first electrode disposed about 180° relative to a second electrode, and the second pair of electrodes comprises a third electrode disposed about 180° relative to a fourth electrode.

24. The electrical lead of claim 23, wherein the plurality of electrodes further comprises: a third pair of electrodes comprising a fifth electrode disposed about 180° relative to a sixth electrode.

25. The electrical lead of claim 24, wherein the plurality of electrodes further comprises: a fourth pair of electrodes comprising a seventh electrode disposed about 180° relative to an eighth electrode.

26. The electrical lead of claim 25, wherein the second pair of electrodes is rotated 90° relative to the first pair of electrodes, the third pair of electrodes is rotated 90° relative to the second pair of electrodes, or the fourth pair of electrodes is rotated 90° relative to the third pair of electrodes.

27. The electrical lead of claim 24, wherein the first pair of electrodes and the third pair of electrodes are circumferentially aligned.

28. The electrical lead of claim 25, wherein the second pair of electrodes and the fourth pair of electrodes are circumferentially aligned.

* * * * *